United States Patent [19]
Pumphrey et al.

[11] Patent Number: 4,687,336
[45] Date of Patent: Aug. 18, 1987

[54] MEASUREMENT OF OPTICAL DENSITY VIA NEPHENOMETRY

[75] Inventors: John G. Pumphrey, Lewisville; Robert E. Shanks, Grapevine, both of Tex.

[73] Assignee: Abbott Laboratories, North Chicago, Ill.

[21] Appl. No.: 708,471

[22] Filed: Mar. 5, 1985

[51] Int. Cl.⁴ .............................................. G01N 21/00
[52] U.S. Cl. .................................... 356/436; 356/338; 356/440; 356/442
[58] Field of Search ............... 356/337, 338, 339, 340, 356/341, 342, 343, 432, 433, 434, 435, 436, 442, 440

[56] References Cited

U.S. PATENT DOCUMENTS

| | | | |
|---|---|---|---|
| 3,450,886 | 6/1969 | Lown | 356/341 |
| 3,967,901 | 7/1976 | Rodriguez | 356/338 |
| 4,475,816 | 10/1984 | Mooradian | 356/338 |

Primary Examiner—R. A. Rosenberger
Attorney, Agent, or Firm—Martin L. Katz; Donald L. Corneglio

[57] ABSTRACT

A method for measuring the formation of optical density at 350 to 700 nm in a material is disclosed. The method comprises directing through a solution of the material with light-scattering means suspended therein a beam of light having a wavelength in the range of 350 to 700 nm at which the material absorbs light, and measuring the scattered intensity of the light leaving the solution at a given angle.

5 Claims, 6 Drawing Figures

MEASUREMENT OF OPTICAL DENSITY VIA NEPHENOMETRY

BACKGROUND OF THE INVENTION

1. Field of the Invention

This invention relates to the indirect measurement of optical density, and to the use of the measurement to assay solutions of a material which imparts optical density at a given wavelength or band of wavelengths. The actual measurement that is made is of scattered energy intensity; the ratio of two of these intensities has been found to be a function of optical density or absorbance.

2. The Prior Art

So far as is known, the measurement of scattered energy intensity has not heretofore been used to determine optical density. Scattered energy intensity measurements have been made, in reducing the instant invention to practice, using a retrofitted "TDx", a registered trademark, instrument that is commercially available from Abbott Laboratories. The instrument, insofar as its use is relevant to the instant invention, comprises a light scattering accessory carousel which carries twenty cuvettes for samples to be investigated, automatic pipetting means for adding material to the cuvettes, and a sensor for measuring the intensity of light energy leaving each of the cuvettes in succession as the carousel is rotated from position to position. The original instrument also includes means to excite samples in the cuvettes with light of a particular wavelength, but this means plays no part in the practice of the instant invention; its purpose in the original instrument is to excite a sample, causing luminescence or fluorescence. The measured intensity of the energy leaving a cuvette as a consequence of the luminescence or fluorescence could be used in analytical work, for example to determine the concentration of the luminescing or fluorescing material in a sample or to measure the polarization of fluorescence.

Two different instruments were retrofitted for use in practicing the instant invention. In one case light emitting diodes were installed radially inwardly of the first six cuvettes in a carousel for the instrument, and were connected in parallel through a 90 ohm load resistor and a nickel-cadmium 9 volt battery. Each of the diodes was mounted to direct a beam of light through a sample in the adjacent cuvette; the axis of the beam of light was in the same plane as the axis of the sensor for the detection of scattered light intensity and at an angle of 37.5° thereto. In the other case, a standard carousel for the instrument was modified so that an inner portion of the base remained stationary while the rest of the carousel (including the 20 cuvettes) rotated therearound during operation of the instrument. A single light emitting diode and a constant voltage regulator circuit were installed upon the stationary base. The circuit included a load resistor and a lithium battery. The light emitting diode was so positioned that the axis of the light beam therefrom was in the same plane as the axis of the sensor for the detection of scattered light intensity and at an angle of 37.5° thereto. When the carousel was rotated, successive ones of the cuvettes were positioned for the light beam to be directed therethrough.

BRIEF DESCRIPTION OF THE INSTANT INVENTION

The instant invention is based upon the discovery that the ratio of two energy intensity measurements made with the retrofitted instrument described above is a function of the optical density of any of several materials present in samples used in making the measurements; as is well known, such optical density varies as a function of concentration of the materials. The diodes in the retrofitted instrument emit light at a wavelength of substantially 565 nm; polystyrene microspheres added to the samples cause scattering of the incident light. The materials whose solutions evidence the indicated phenomenon all absorb light at 565 nm. The phenomenon is believed to occur because the solutions absorb the 565 nm light from the diode to an extent which varies as a direct function of the concentration of the materials in the samples, causing consequent changes in the scattered energy intensity measured by the sensor of the instrument.

The measurements that are made in practicing the instant invention are both "excess scattered energy intensities", which term is used herein to mean a given scattered energy intensity measurement minus the measured background energy intensity; the latter can be measured in the relevant cuvette, when appropriately positioned for a beam of light from an energized LED to pass therethrough and the cuvette contains only distilled water or a buffer. A given quantity of a turbidity standard, for example polystyrene microspheres suspended in water, and having diameters less than 1.0 micron (such that the suspensions are stable indefinitely), can then be added to the cuvette and a second energy intensity determined. The magnitude of the second intensity reading is influenced by the scattering of the light from the LED which is caused primarily by the microspheres. The excess scattered energy intensity when only the buffer or distilled water and the microspheres are present, Is(1), is the second measured intensity minus the measured background intensity. A given quantity of a solution of a material being investigated and microspheres to maintain a constant proportion are next added to the cuvette, and a third scattered energy intensity measurement is made. The material must be one which absorbs energy incident upon and scattered by the microbeads (565 nm light in the case of the retrofitted instrument that has been described). The excess scattered energy intensity for the solution of the material under investigation, Is(2), is the third intensity reading minus the measured background intensity. The ratio that has been found to vary as an inverse function of concentration is Is(2)/Is(1). In many instances the background intensity is small relative to the scattered intensities, and can be ignored, and the two scattered energy measurements can be treated as Is(1) and IS(2).

From a consideration of the optics involved it has been theorized that, to a first order approximation, $$\ln[Is(2)/Is(1)] = -2Er$$

where E is the absorbance of the sample under investigation and r is the radius of the cuvette. This first order approximation neglects the effects of multiple scattering and of the physical dimensions of the light beam. The experimental evidence demonstrates that a plot of $-\ln[Is(2)/Is(1)]$ versus solution concentration is likely to approach, but not to reach, a straight line. A plot of $Is(2)/Is(1)$ versus solution concentration, on the other hand, is likely to be farther from a straight line.

OBJECTS OF THE INVENTION

Figure 1:
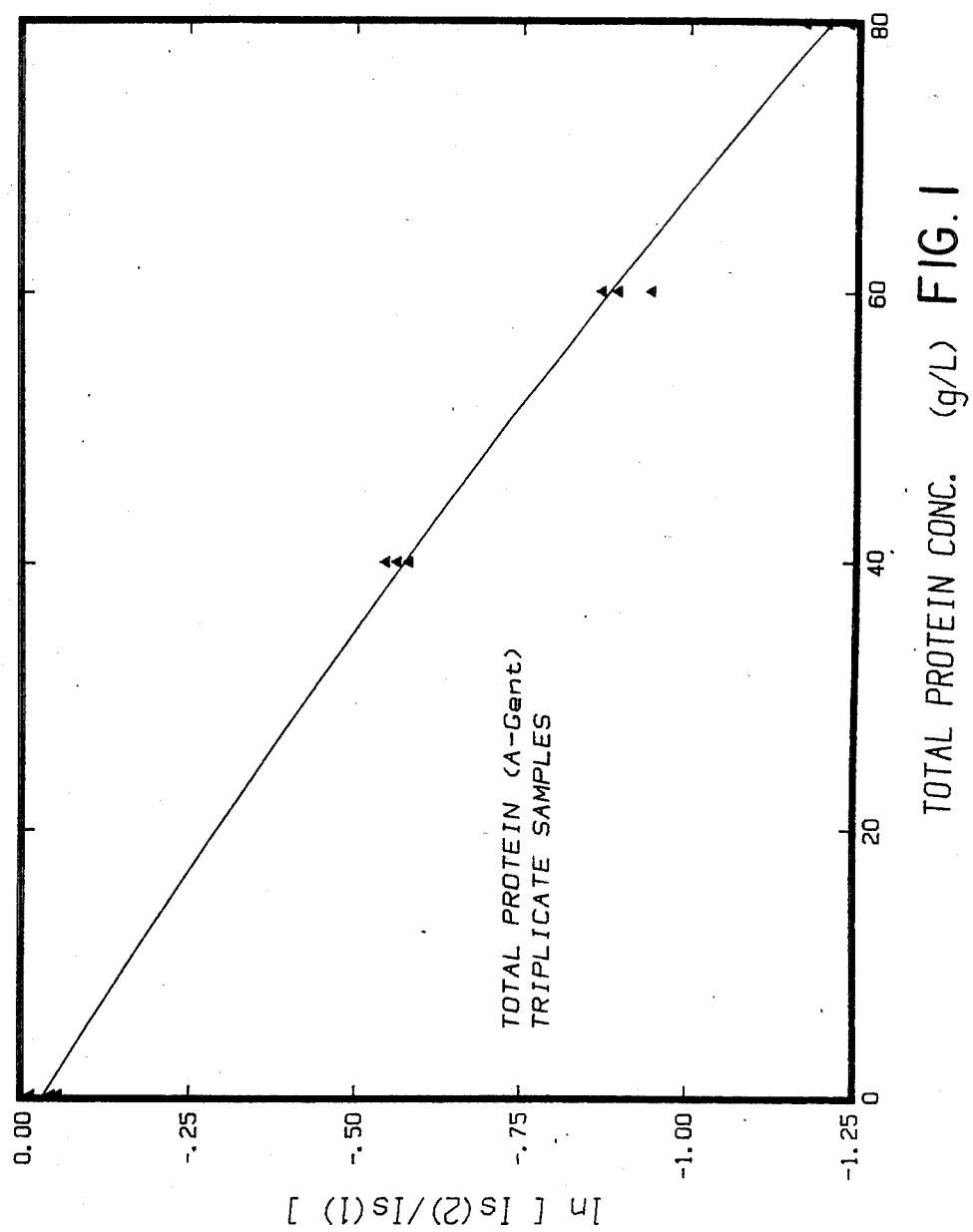
FIG. 1 is a plot of ln [Is(2)/Is(1)] for saline solutions of protein against protein concentrations in the solutions.

It is an object of the instant invention to provide a method for determining the optical density of a solution.

It is another object of the invention to provide a method for determining the scattered energy attenuation attributable to a given sample of a material.

It is still another object of the invention to provide a method for determining a ratio of two scattered energy intensities which varies as a function of the concentration of a solution used in measuring one of the intensities.

Other objects and advantages will be apparent from the description which follows, reference being made to the accompanying drawings and to the following Examples.

DESCRIPTION OF THE PREFERRED EMBODIMENTS

The procedures described in the following Examples constitute the best mode presently contemplated by the inventors. The Examples differ from one another only with respect to the identity of the materials involved. Since this identity is not a part of the invention, it being necessary only that the material absorb light of the wavelength used in practicing the method, the Examples, jointly, constitute a single mode.

The background scattered intensity was found to be negligible under the experimental conditions used in these Examples and, therefore, the actual scattered energy intensity measurements were used, and are reported herein as Is(1) and Is(2).

The following Example describes an assay of total protein.

EXAMPLE 1

Each of three cuvettes of the retrofitted instrument described above (fitted with only a single, stationary LED) was charged with 800 uL of a "Suspension A" of polystyrene microbeads and 200 uL distilled water, and, after thorough mixing, an intensity reading was taken with the diode energized. Each of the three cuvettes was then charged with 800 uL of Suspension A and 200 uL standard solution of bovine albumin fraction V in normal saline solution preserved in 0.05 percent sodium azide, and after thorough mixing and incubation for five minutes at 35° C., a second intensity reading was taken, again, with the LED energized. The standard solution contained 40 grams per liter of the bovine albumin fraction. The measured scattered energy intensities and the ratios are set forth in Table I, below, together with the calculated average ratio, the calculated Variance in ratio and the Coefficient of Variation of the ratio (the intensities reported herein are in arbitrary units of "counts"):

TABLE I

| Cuvette No. | Is(1) | Is(2) | Is(2)/Is(1) |
|---|---|---|---|
| 1 | 6155 | 3532 | 0.574 |
| 2 | 5218 | 2902 | 0.556 |
| 3 | 5193 | 2990 | 0.575 |
| Average | | | 0.568 |
| Calculated Standard Deviation | | | 0.011 |
| Coefficient of Variation | | | 1.94% |

The procedure described above was repeated except that the protein content of the standard solution was varied from 0 (solvent only), to 60 g per L and to 80 g per L. Is(1), Is(2) and the ratio of Is(1) to Is(2) are set forth in Table II, below:

TABLE II

| | | Replicate No. | | |
|---|---|---|---|---|
| | | 1 | 2 | 3 |
| 0 Protein | Is(1) | 6131 | 6127 | 5214 |
| | Is(2) | 5873 | 5914 | 5181 |
| | Is(2)/Is(1) | 0.958 | 0.965 | 0.994 |
| 60 g per L Protein | Is(1) | 6112 | 5229 | 5215 |
| | Is(2) | 2363 | 2145 | 2193 |
| | Is(2)/Is(1) | 0.386 | 0.410 | 0.420 |
| 80 g per L Protein | Is(1) | 6159 | 6142 | 5192 |
| | Is(2) | 1909 | 1803 | 1578 |
| | Is(2)/Is(1) | 0.310 | 0.293 | 0.304 |

Suspension A of polystyrene microbeads was prepared by diluting a latex containing 10 grams of the polystyrene beads per deciliter to a bead concentration of 0.5 gram per deciliter with A-Gent ® Total Protein Reagent (List No. 6027-02, Abbott Laboratories, South Pasadena, Calif. The polystyrene beads had an average diameter of 0.85 um.

The protein standard solutions used as described above in Example 1 were solutions in distilled water which also contained 0.9 g/dL NaCl and 0.05 g/dL NaN$_3$.

The data of Example 1 are presented graphically in FIG. 1 of the attached drawings. It will be appreciated from the graphic presentation of the data that the method of Example 1 is a useful analytical technique which can be employed, after a calibration curve similar to FIG. 1 has been prepared for any given instrument, for the rapid determination of total protein in unknown samples.

The following Example describes an assay of calcium.

EXAMPLE 2

Substantially the procedure described in Example 1, above, was used to determine Is(1) and Is(2) for each of three different calcium standards. The standards were aqueous solutions, all of which contained 2 mg/dL magnesium, a trace of HCl and calcium; the calcium content, as CaCO$_3$, was 8 mg/dL in one case, 10 mg/dL in another and 12 mg/dL in the third. The standards were "A-Gent" ® calcium, List No. 6220-02 reconstituted in accordance with instructions furnished by the supplier, Abbott Laboratories. A polystyrene microbead suspension (hereafter "Suspension B") used in carrying out the procedures described in this Example was prepared by diluting to 20 mL, 10 uL of a polystyrene bead suspension containing 8.2 g microbeads per deciliter with A-Gent ® Calcium Reagent (List No. 6064-02, Abbott Laboratories, South Pasadena, Calif.); the microbeads had an average diameter of 0.5 micron. Intensity readings were take with 900 uL of Suspension B and 100 uL distilled water in each of the cuvettes, and with an additional 900 uL aliquot of Suspension B and 100 uL of one of the foregoing calcium standard solutions. The cuvette contents were mixed well before the intensity readings were taken, and incubation for five minutes at 35° C. was allowed after addition of the standard calcium solutions and the subsequent mixing. Is(1), Is(2) and the ratio of Is(2) to Is(1) are set forth in Table III, below:

TABLE III

|  |  | Replicate No. | |
|---|---|---|---|
|  |  | 1 | 2 |
| 0 Ca | Is(1) | 3073 | 3060 |
|  | Is(2) | 3069 | 3024 |
|  | Is(2)/Is(1) | 0.999 | 0.988 |
| 8 mg per dL Ca | Is(1) | 3053 |  |
|  | Is(2) | 1745 | ND* |
|  | Is(2)/Is(1) | 0.572 |  |
| 10 mg per dL Ca | Is(1) | 3050 |  |
|  | Is(2) | 1438 | ND |
|  | Is(2)/Is(1) | 0.471 |  |
| 12 mg per dL Ca | Is(1) | 3070 | 3059 |
|  | Is(2) | 1221 | 1221 |
|  | Is(2)/Is(1) | 0.398 | 0.399 |

*ND means not done

Figure 2:
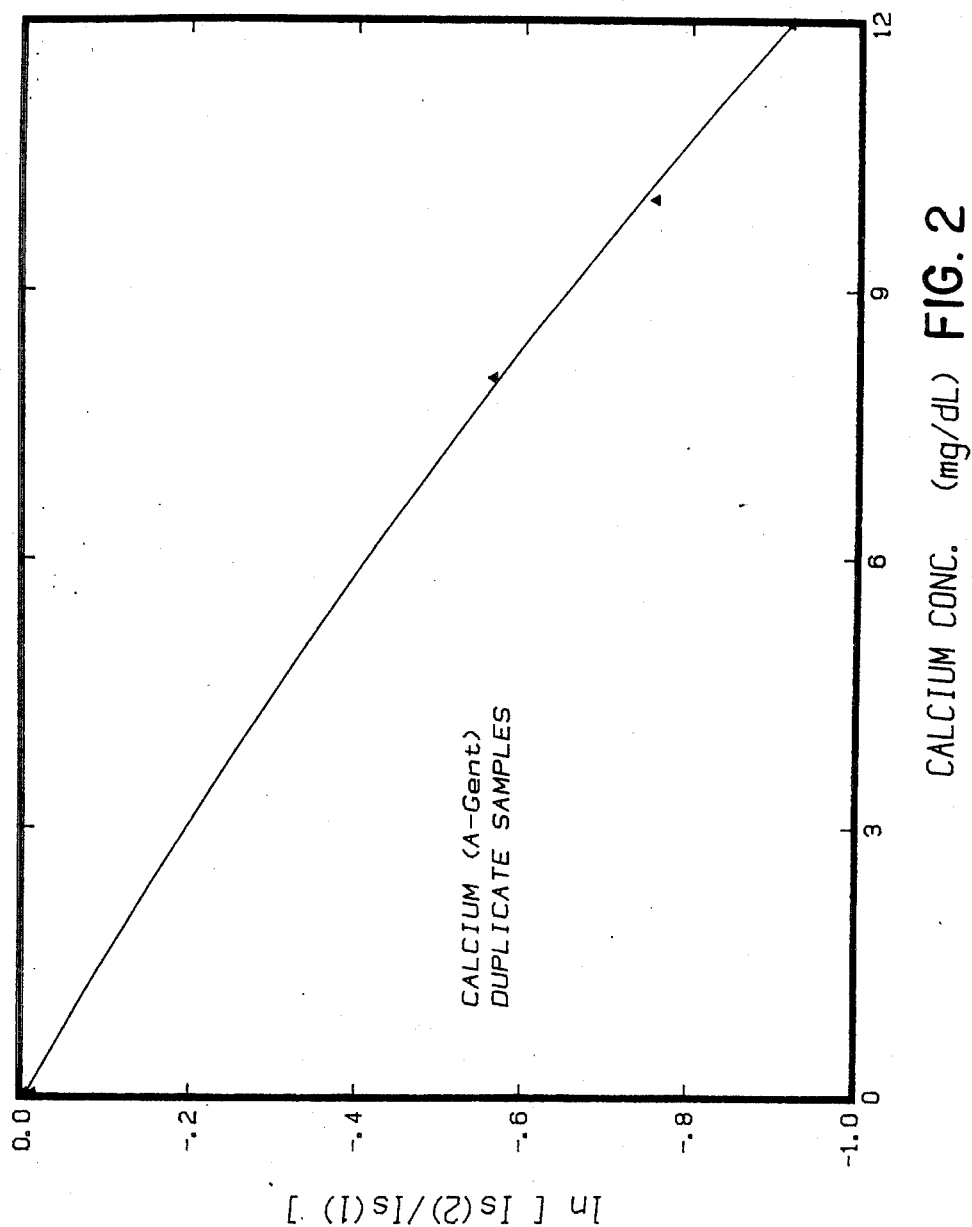
FIG. 2 is a plot of ln [Is(2)/Is(1)] for aqueous calcium solutions against calcium concentration therein.

The data of Example 2 are presented graphically in FIG. 2 of the attached drawings.

The following Example describes a cholesterol assay.

EXAMPLE 3

Substantially the procedure described in Example 1, above, was used to determine Is(1) and Is(2) for each of three different standard cholesterol reagents. The reagents were aqueous solutions of cholesterol, with wetting agents and preservatives, containing 100, 300 and 400 mg/dL cholesterol. The reagent solutions were reconstituted "A-Gent" ® Cholesterol, List No. 6036-02, reconstituted in accordance with instructions furnished by the supplier, Abbott Laboratories. A polystyrene microbead suspension (hereafter Suspension "C") used in carrying out the procedures described in this Example was prepared by diluting to 20 mL, ten uL of a polystyrene bead suspension containing 8.2 g microbeads per deciliter with A-Gent ® Cholesterol Reagent (List No. 6095-01, Abbott Laboratories, South Pasadena, Calif.); the microbeads had an average diameter of 0.5 micron. Intensity readings were taken in each of three cuvettes, with 980 uL of Suspension B and 20 uL water, and with an additional 980 uL aliquot of Suspension C and 20 uL of one of the foregoing cholesterol standard solutions. The cuvette contents were mixed well before the intensity readings were taken, and incubation at 35° C. was allowed after addition of the standard cholesterol solutions and the subsequent mixing. Is(1), Is(2) and the ratio of Is(2) to Is(1) are set forth in Table IV, below:

TABLE IV

|  |  | Replicate No. | | |
|---|---|---|---|---|
|  |  | 1 | 2 | 3 |
| 0 cholesterol | Is(1) | 3272 | 3081 | 3094 |
|  | Ia(2) | 3070 | 2911 | 2910 |
|  | Is(2)/Is(1) | 0.938 | 0.945 | 0.940 |
| 100 mg per dL | Is(1) | 3264 | 3270 | 3099 |

TABLE IV-continued

|  |  | Replicate No. | | |
|---|---|---|---|---|
|  |  | 1 | 2 | 3 |
| cholesterol | Is(2) | 2437 | 2343 | 2300 |
|  | Is(2)/Is(1) | 0.747 | 0.716 | 0.742 |
| 300 mg per dL cholesterol | Is(1) | 3302 | 3102 | ND |
|  | Is(2) | 1564 | 1489 |  |
|  | Is(2)/Is(1) | 0.474 | 0.480 |  |
| 400 mg per dL cholesterol | Is(1) | 3284 | 3110 | 3075 |
|  | Is(2) | 1204 | 1228 | 1200 |
|  | Is(2)Is(1) | 0.366 | 0.395 | 0.390 |

Figure 3:
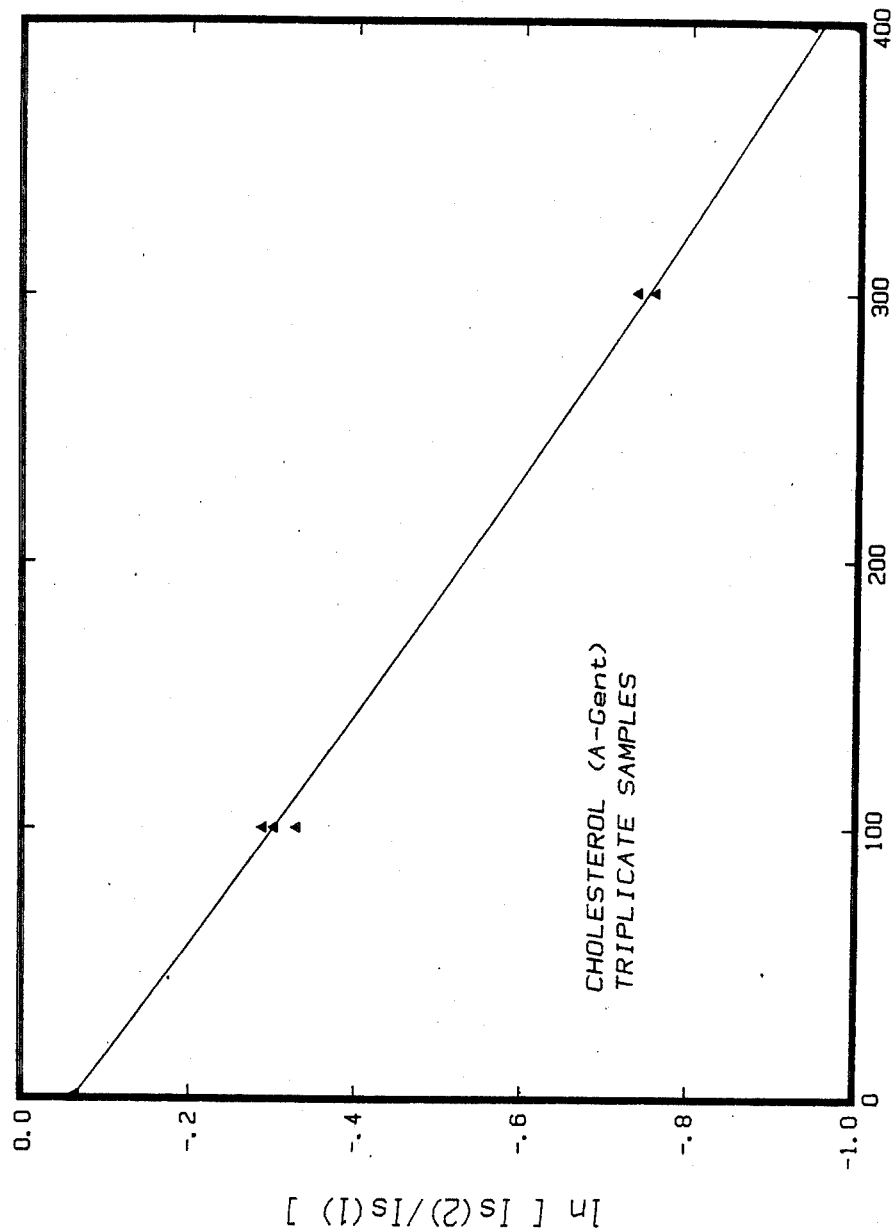
FIG. 3 is a plot of ln [Is(2)/Is(1)] for aqueous cholesterol solutions against concentrations of cholesterol therein.

The data of Example 3 are presented graphically in FIG. 3 of the attached drawings.

The following Example describes an iron assay.

EXAMPLE 4

Substantially the procedure described in Example 1, above, was used to determine Is(1) and Is(2) for each of three different iron standards. The standards were aqueous solutions containing 200, 300 and 500 ug/dL ferric chloride. The standard solutions were made by dissolving weighed pieces of iron wire in hydrochloric acid solution. The pipetting was done automatically in the retrofitted instrument, and involved transfers to and from a predilution cup and a sample cup, in addition to the cuvettes. Two solutions and a dispersion, identified below, were used in preparing the samples:

Polystyrene Latex C, an aqueous dispersion of polystyrene microbeads containing 10 grams of solids per deciliter; the microbeads had an average diameter of 0.85 um.

Solution S, an aqueous 4 molar solution of sodium acetate at pH 6.5 containing, in addition, 3 percent by weight of hydroxylamine and 3 percent by weight of thiourea.

Solution T, an aqueous solution containing 0.7 percent by weight of 3-(2-pyridyl)5,6-diphenyl-1,2,4-triazine-p,p'-disulfonic acid and 5 percent by weight of hydroxyl amine.

Buffer A, a solution in distilled water of 1-10th molar sodium monohydrogen phosphate, pH 7.5.

The predilution cup was charged with 100 uL of Polystyrene Latex C and 125 uL distilled water. The following additions were then made to the predilution cup:

(a) 125 uL of one of the iron standards.
(b) 100 uL Buffer A.
(c) 50 uL Solution S.
(d) 100 uL Buffer A.

A 175 uL portion of the contents of the predilution cup and 825 uL Buffer A were then added to one of the cuvettes and a scattered intensity reading was taken in that cuvette. It will be noted that the cuvette contained the iron standard when this intensity reading was taken; nevertheless, this reading constituted Is(1) because the color which causes scattered light attentuation in this procedure is that formed by reaction between the disulfonic acid of Solution T, which is a chromophore, and the iron of the standard. The iron standard was added to the cuvette before Is(1) was measured so that this measurement would be decreased by any attenuation attributable to the yellow color of the iron standard and the attenuation indicated by the difference between Is(1) and Is(2) would be only that attributable to the color imparted to the iron present in the standard by reaction with the chromophore.

A 175 uL portion of the remaining contents of the predilution cup, a 25 uL charge of Solution T and 800 uL of Buffer A were then charged to the relevant cuvette and a scattered energy measurement was made. Is(1), Is(2) and the ratio Is(2)/Is(1) are set forth in Table V, below:

TABLE V

|  | Is(1) | Is(2) | Is(2)/Is(1) |
|---|---|---|---|
| 0 iron | 7167 | 7003 | 0.977 |
| 200 Mg/dL iron | 7185 | 6562 | 0.913 |
| 300 Mg/dL iron | 7217 | 6250 | 0.866 |
| 500 Mg/dL iron | 7151 | 5674 | 0.793 |

Figure 4:
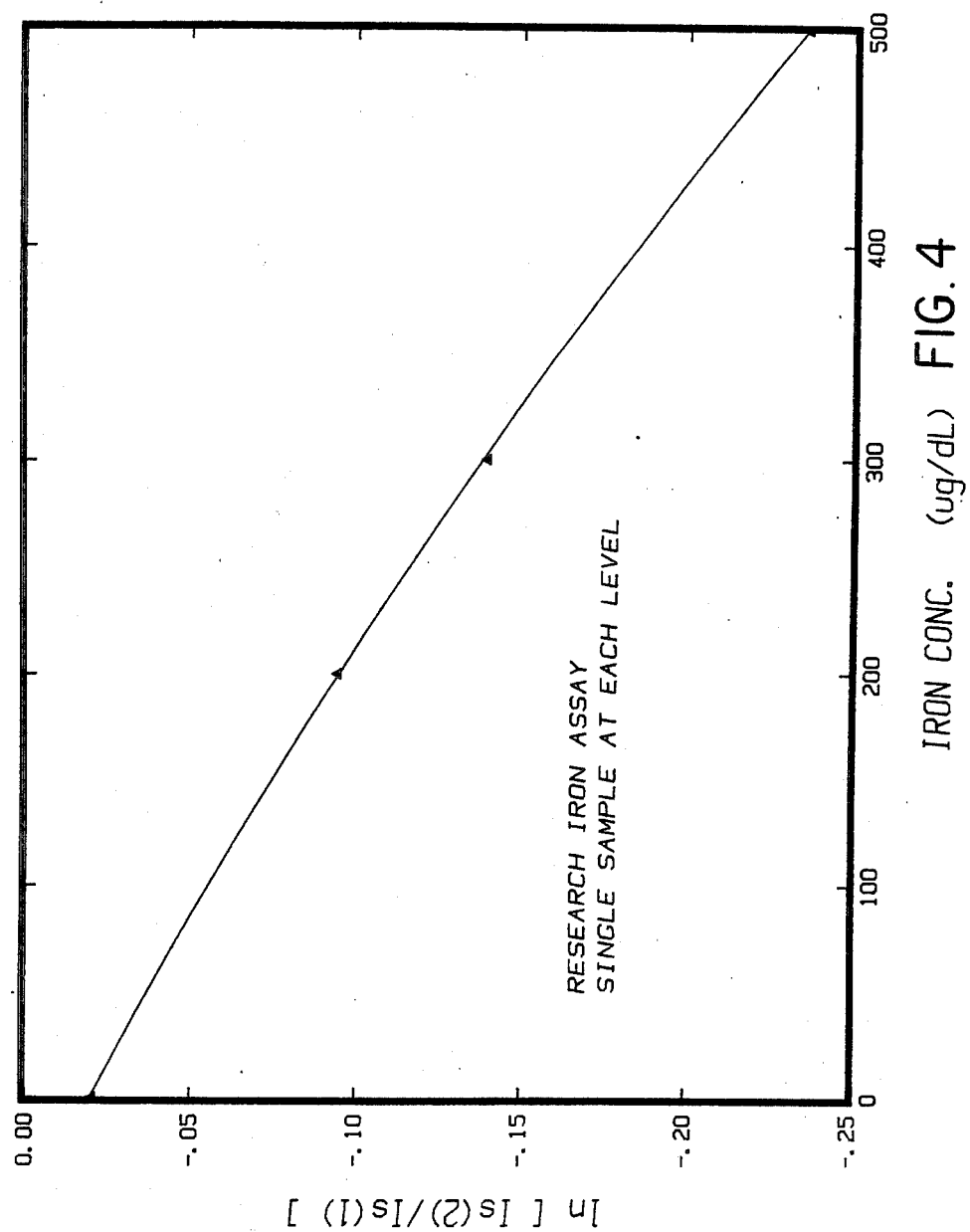
FIG. 4 is a plot of ln [Is(2)/Is(1)] for aqueous solutions of iron versus concentrations of iron therein.

The data of Example 4 are presented graphically in FIG. 4 of the attached drawings.

The following Example describes a bilirubin (total) assay.

EXAMPLE 5

Substantially the procedure described in Example 1, above, was used to determine Is(1) and Is(2) for each of three different bilirubin standard solutions. The solutions were reconstituted bilirubin standards which are available from Sigma Chemical Co., Catalog Nos. B2764, B2889 and B3014 containing, respectively, 2.2, 10.0 and 15.2 mg/dL bilirubin. A polystyrene microbead dispersion, hereafter "Dispersion C", used in carrying out the procedure of this Example 5, was prepared by mixing 45.0 ml "Total Bilirubin Reagent" with 1.5 ml "Sodium Nitrite Solution" and carboxylated polystyrene beads to produce a suspension containing 0.03 percent by weight of the beads. "Total Bilirubin Reagent" is commercially available from Sigma Chemical Co., Catalog No. 550-4; it is a solution of 0.1 percent by weight of sulfanilic acid, 50 percent by weight of dimethylsulfoxide and an added stabilizer in 0.2 normal hydrochloric acid. "Sodium Nitrite Solution" is commercially available from Sigma Chemical Co., Catalog No. 550-7; it is an aqueous sodium nitrite solution containing 0.07 gram mole per liter of $NaNO_3$. The carboxylated polystyrene beads had an average diameter of 0.038 uM.

Intensity readings were taken in each of five cuvettes, with 900 uL Suspension C and 100 uL water, and with an additional 900 uL aliquot of Suspension C and 100 uL of one of the bilirubin standards. The contents of the cuvette were mixed thoroughly and allowed to incubate five minutes at 35° C. Before each intensity reading. Is(1), Is(2) and the ratio of Is(2) to Is(1) are set forth in Table VI, below:

TABLE VI

|  | Replicate No. | | | | |
|---|---|---|---|---|---|
|  | 1 | 2 | 3 | 4 | 5 |
| 0 Bilirubin |  |  |  |  |  |
| Is(1) | 9154 | 11402 | 8019 | 9383 | 11363 |
| Is(2) | 9179 | 11400 | 8288 | 9306 | 11073 |
| Is(2)/Is(1) | 1.00 | 1.00 | 1.03 | 0.99 | 0.97 |
| 2.2 mg/dL bilirubin |  |  |  |  |  |
| Is(1) | 9139 | 8022 | 9419 | 11445 | 11428 |
| Is(2) | 8692 | 7702 | 8963 | 11092 | 10934 |
| Is(2)/Is(1) | 0.95 | 0.96 | 0.95 | 0.97 | 0.96 |
| 10.0 mg/dL bilirubin |  |  |  |  |  |
| Is(1) | 9116 | 9200 | 8024 | 8040 | 9413 |
| Is(2) | 3946 | 3858 | 3459 | 3549 | 3802 |
| Is(2)/Is(1) | 0.43 | 0.42 | 0.43 | 0.44 | 0.40 |
| 15.2 mg/dL bilirubin |  |  |  |  |  |
| Is(1) | 9125 | 11300 | 9517 | 9445 | 8010 |
| Is(2) | 2016 | 2771 | 2077 | 2050 | 1975 |
| Is(2)/Is(1) | 0.22 | 0.25 | 0.22 | 0.22 | 0.25 |

Figure 5:
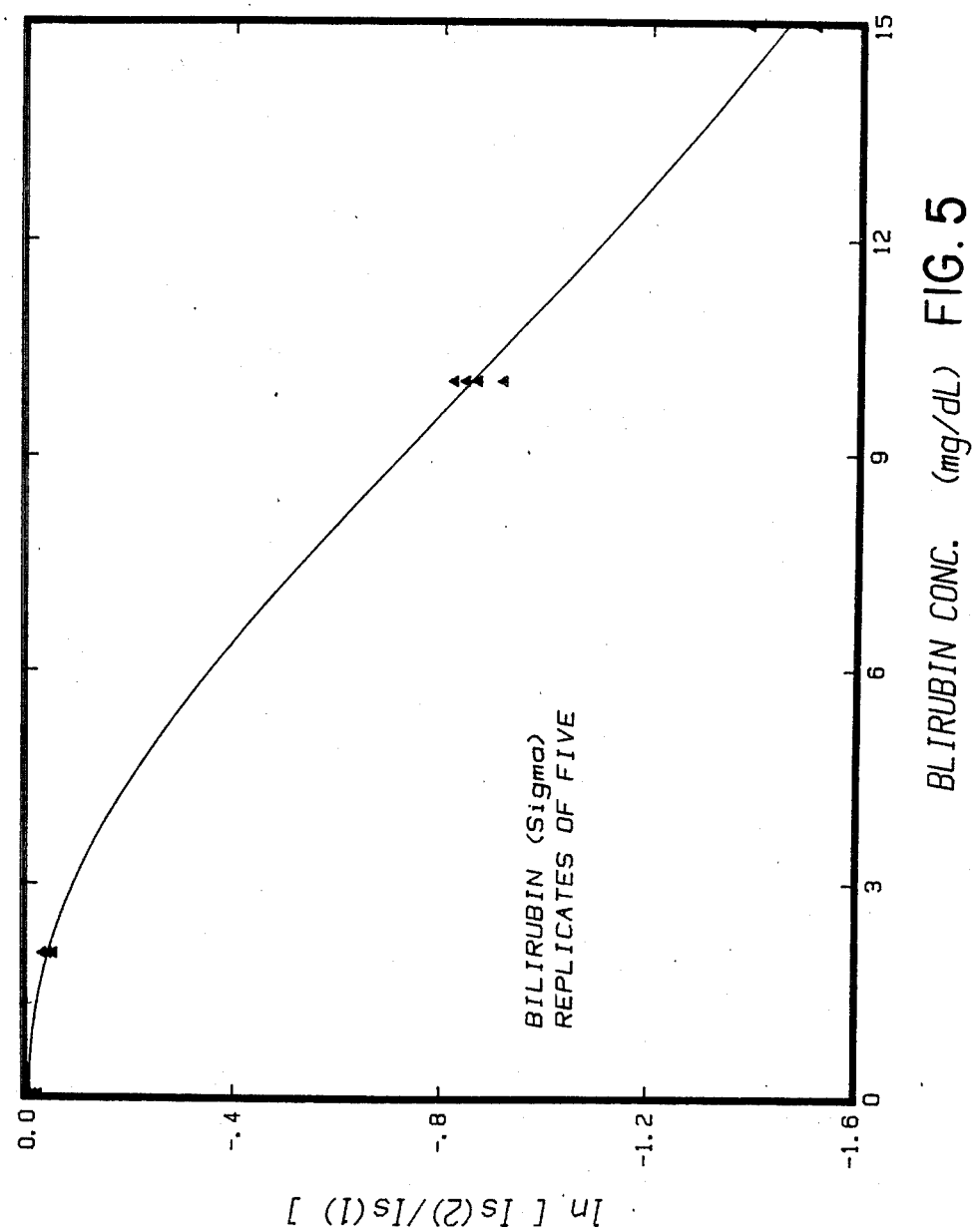
FIG. 5 is a plot of ln [Is(2)/Is(1)] for solutions of bilirubin in a buffered bovine albumin base versus concentrations of bilirubin therein.

The data of Example 5 are presented graphically in FIG. 5 of the attached drawings.

The formation of optical density at 565 nm was measured in the foregoing Examples. This was convenient because the instrument which was retrofitted to make the measurements had a sensor for measuring energy intensity at substantially 565 nm. Consequently, LEDs were selected which had a center wavelength of 565 nm and were used with a cutoff emission filter centered at about 525 nm and materials were selected which form optical density at wavelengths around 565 nm. It will be appreciated, however, that the formation of optical density at any desired wavelength, say in the range of 350 to 700 nm, could be measured by changing the filters in the energy intensity measuring portion of the instrument to pass light of the desired wavelength and to remove light of undesired wavelengths and by making a corresponding change in the wavelength of the light beam passed through the solution. It is usually preferred that the formation of optical density be measured using light of a relatively narrow band of wavelengths, say not greater than 20 nm and, preferably, not greater than 15 nm, as interference from incidental impurities is minimized in this way. However, the formation of optical density can be measured in accordance with the invention in a broad band of wavelengths, or even in the entire spectrum of 350 to 700 nm.

Similarly, polystyrene microbeads were used in the procedures of all of the Examples to cause scattering of the light beam in the sample. Other means could be used, but microbeads, usually of polystyrene, are preferred because they are in general use and are widely available and accepted.

Finally, in the foregoing Examples, all measurements of excess scattered intensity of the light leaving the solution were made with the beam directed at an angle of 37.5° to the axis of the energy intensity sensor. It will be appreciated from the accompanying drawings that this angle was eminently satisfactory because the curves that were generated are admirably suitable for use in making assays. However, any other given angle could be used, and the quantity, size, or both of the microbeads employed could be increased or decreased if necessary to increase or decrease the scattered energy intensity at the different angle selected. It is well known, however, that small angles, usually 15° to 55°, are preferred for sensitive light scattering measurements.

Figure 6:
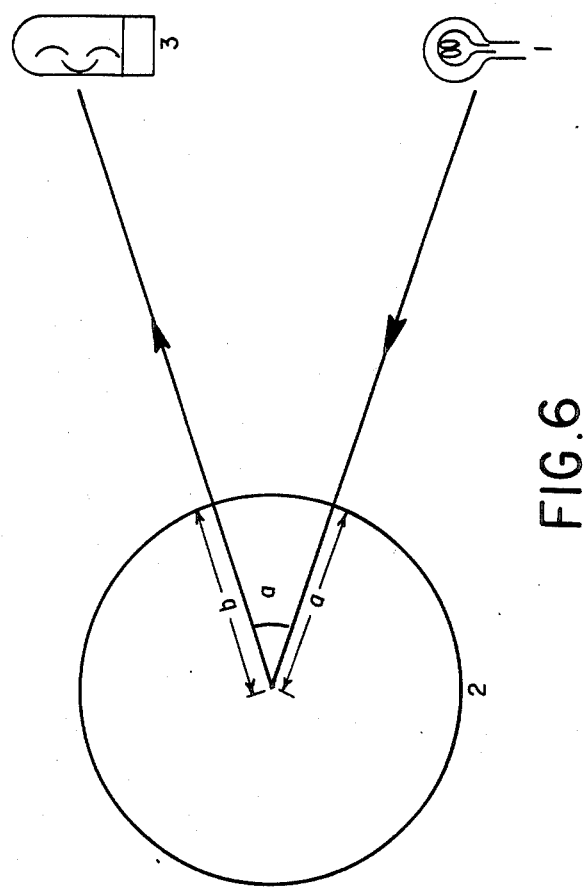
FIG. 6 is a schematic of the method and associated apparatus.

In its essential details (FIG. 6), the instant invention is a method for measuring the formation of optical density at wavelengths of 350 to 700 in a material. The method comprises directing a beam of light (a) from a light source (1) having a wavelength in the range of 350 to 700 nm through a solution of the material in a curvette (2) with light scattering means suspended therein, and measuring the excess scattered intensity of the light (b) leaving the solution at a given angle (a). In a preferred embodiment, the excess scattered intensity of the light leaving the solution at a given angle (a) is measured by a light sensor (3), and the ratio thereof to the excess scattered intensity of the same light leaving an optically identical system at the same angle, except that the solution of the material is not present, is determined.

It will be apparent that various changes and modifications can be made from the details of the invention as described herein without departing from the spirit and scope of the appended claims.

We claim:

1. A method for measuring the formation of optical density at 350 to 700 nm in a material, said method comprising (a) directing through a first sample which includes a solution of the material and a light-scattering means suspended therein, a first beam of light having a wavelength in the range of 350 to 700 nm at which the material absorbs light, (b) measuring the scattered intensity of the light leaving the first sample at a given angle, (c) directing a beam of light having characteristics at least substantially the same as those of the first beam through a second sample which, optically, is substantially identical to the first sample except that the solution of the material which absorbs light at the indicated frequency is not present, (d) measuring the scattered intensity of the light leaving the second sample at the given angle, and (e) comparing the measurements of scattered intensity from steps (b) and (d).

2. The method as claimed in claim 1 for measuring the formation of optical density at 350 to 700 nm in a material, which method includes the additional steps of (f) directing a beam of light having characteristics at least substantially the same as those of the first beam through a blank which, optically, is substantially identical to the first sample except that neither the solution of the material nor the light-scattering means is present, (g) measuring the intensity of the light leaving the blank at the given angle, and (h) comparing the measurements of scattering intensity from steps (b), (d) and (g).

3. A method for measuring the formation of optical density at 350 to 700 nm, said method comprising (a) placing in a sample container which is transparent to energy having a wavelength between 350 and 700 nm a suspension of a given weight per mL of light-scattering means, (b) energizing a source to direct a beam of light having a wavelength in the range of 350 to 700 nm along a given path through the suspension, (c) measuring the scattered intensity of the light leaving the suspension at a given angle, (d) adding to the suspension a solution of a material which absorbs light at the 350 to 700 nm frequency and any additional quantity of the light-scattering means to produce a solution of the material having the given weight per mL of the light-scattering means as in step (a), (e) energizing the source to direct a beam of light along substantially the same given path through the suspension prepared in step (d), (f) measuring the scattered intensity of the light leaving the suspension at the given angle, and (g) comparing the measurements of scattering intensity from steps (c) and (f).

4. The method as claimed in claim 3 for measuring the formation of optical density at 350 to 700 nm in a material, which method includes the additional steps of (h) directing a beam of light from the source through a blank which, optically, is substantially identical to the sample except that neither the solution of the material nor the light-scattering means is present, (i) measuring the intensity of the light leaving the blank at the given angle, and (j) comparing the measurements of scattering intensity from steps (c), (f) and (i).

5. A method as claimed in claim 3 wherein the suspension of light scattering means which is placed in the sample container includes a dissolved material which is reactive with a second material to produce a reaction product that is soluble in the dispersion and absorbs light of the frequency furnished by the source, and wherein the second material and additional light-scattering means are added to the sample container after the first measurement of scattered light intensity to produce the reaction product before the second measurement of scatter light intensity.

* * * * *